United States Patent [19]

Minnich

[11] Patent Number: 5,119,814
[45] Date of Patent: Jun. 9, 1992

[54] METHOD AND APPARATUS FOR MONITORING BLOOD LOSS VIA RETINAL VENOUS OXYGEN SATURATION

[76] Inventor: Thomas E. Minnich, 868 Summerhill Dr., Friendsville, Tenn. 37737

[21] Appl. No.: 558,082

[22] Filed: Jul. 25, 1990

[51] Int. Cl.⁵ .............................................. A61B 5/00
[52] U.S. Cl. ................................... 128/633; 128/666; 128/691; 356/41; 351/221
[58] Field of Search ....................... 351/221, 205, 206; 356/41; 128/633, 666, 745, 691

[56] References Cited

U.S. PATENT DOCUMENTS

| | | | |
|---|---|---|---|
| 4,166,695 | 9/1979 | Hill et al. | 128/745 |
| 4,253,744 | 3/1981 | Sawa | 351/211 |
| 4,305,398 | 12/1981 | Sawa | 128/666 |
| 4,485,820 | 12/1984 | Flower | 128/633 |
| 4,579,430 | 4/1986 | Bille | 128/691 |
| 4,838,683 | 6/1989 | Ichihashi et al. | 128/633 |
| 4,877,322 | 10/1989 | Hill | 128/633 |
| 4,922,919 | 5/1990 | Novack | 128/633 |
| 4,941,741 | 7/1990 | Mizuta | 351/221 |

OTHER PUBLICATIONS

"The choroidal eye oximeter: An instrument for measuring oxygen saturation of blood in vivo," Laing et al., *IEEE Transactions on Biomedical Engineering*, May 1975, vol. BME-22, No. 3, pp. 183-195.

*Primary Examiner*—Ruth S. Smith
*Assistant Examiner*—Robert L. Nasser, Jr.
*Attorney, Agent, or Firm*—Pitts and Brittian

[57] ABSTRACT

A non-invasive retinal scanning system which monitors internal blood loss. A portion of the ocular fundus is illuminated, in an annular fashion, with two wavelengths of light, one of which serves as a reference. Scanning the fundus circumferentially enables retinal venous blood to be detected, which corresponds to desaturated hemoglobin. The intensity of light reflected from the retinal vein is detected and converted to an electronic signal proportional to the value of oxygen saturation of venous hemoglobin, which becomes the value of interest. Thus, a decline in venous oxygen saturation over time correlates linearly with progressive internal bleeding.

6 Claims, 3 Drawing Sheets

METHOD AND APPARATUS FOR MONITORING BLOOD LOSS VIA RETINAL VENOUS OXYGEN SATURATION

DESCRIPTION

1. Technical Field

The present invention relates to the medical practice of monitoring blood loss. More specifically the invention relates to a non-invasive method for measuring oxygen saturation of venous hemoglobin by reflectance spectrophotometry.

2. Background Art

The level of desaturated hemoglobin is a sensitive parameter to assess the rate and estimate the quantity of internal hemorrhage over time. The earliest studies correlating venous oxygen saturation with blood loss were conducted by Sheldon, et al., in an article entitled "Continuous $SvO_2$ and Other New Hemodynamic Parameters As Early Indicators of Hypovolemia" in *Continuous Measurement of Blood Oxygen Saturation in the High Risk Patient*, Oximetrix, Inc., Vol. 1:67–79, 1986. Utilizing the dog model, Sheldon continuously monitored venous oxygen saturation in both the pulmonary artery and peripheral vein, using the Oximetrix reflectance spectrophotometry catheter.

Normally, the hemoglobin in veins is 75% saturated with oxygen. This provides a reserve of oxygen for critical states such as hemorrhage or heart attack, when more oxygen must be extracted by body organs. Thus, during bleeding states, the capillary red blood cells unload more oxygen into tissues, resulting in a lower, postcapillary, venous oxygen saturation. As the canines in Sheldon's study were bled to a pressure of 40 mm Hg, both central (pulmonary artery) and peripheral venous oxygen saturation fell. Blood was reinfused into the dogs, and the levels of venous hemoglobin saturation returned to baseline. Sheldon found that oxygen saturation in the veins declines in a linear fashion when hemorrhage occurs. The additional implication of this study is that regardless of the region of the body that bleeding occurs, any central or peripheral venous site will reflect the magnitude of hemorrhage.

The present invention utilizes the retinal vein as the monitoring site. This was chosen because it is the most accessible peripheral vein for non-invasive study. Prior to this invention, published studies which monitored venous oxygen saturation during hemorrhage employed catheters to accomplish this, such as those inserted into the subclavian vein or forearm vein. The attendant complications of these invasive procedures include bleeding, infection and, in the subclavian site, the potential for pneumothorax or hemothorax. Furthermore, the insertion of catheters into the central circulation of the conscious patient is stressful, particularly in children.

Current clinical parameters to monitor bleeding are not sensitive enough to detect early, small volume blood loss. The hematocrit may remain normal for over 24 hours as bleeding ensues. The blood pressure will not fall until at least 30% of the total blood volume has been lost. A patient's pulse will not become rapid until 15% of blood volume is lost. Therefore, a non-invasive venous monitoring site and method was needed which would permit detection of 1% or less of total blood volume loss.

Prior art using the eye to measure oxygen saturation focused on different portions of the fundus. In U.S. Pat. No. 4,485,820, Flower disclosed a scleral contact lens with a fiberoptic apparatus which measured the hemoglobin saturation of the choroidal capillaries. This corresponded to the arterial saturation in, primarily, premature infants. Rather than focusing on a small area of the fundus, Flower utilized the capacity of the eye to serve as an integrating sphere, thereby providing the largest possible surface area to monitor choroidal (arterial) oxygen saturation. In patients with normal cardiac and respiratory function, the oxygen saturation of arterial blood remains fairly constant during bleeding, and consequently is not a useful parameter.

In U.S. Pat. No. 4,877,322, Hill described the use of a collimated beam of light to view specific areas of the fundus, such as the macula or optic disc. The ratio of oxyhemoglobin to reduced hemoglobin of these particular areas allows the physician to detect macular degeneration or glaucoma at its early stages.

Novack, in U.S. Pat. No. 4,922,919, measures the oxidative metabolism in ocular tissue by taking advantage of the absorption peak of cytochrome c oxidase. Novack primarily employs an optical probe, which penetrates the ocular body. While Novack describes an alternative apparatus which consists of a contact lens, and subsequently mentions that the invention can also measure desaturated hemoglobin, the retinal vein is not monitored specifically nor is blood loss monitoring discussed.

Accordingly, it is an object of the present invention to provide a non-invasive retinal scanning system for measuring blood loss early, such that a change in the oxyhemoglobin saturation of the vein can be detected when 1% or less of total blood volume has been lost, thus allowing detection of blood loss long before the onset of shock.

It is another object of the present invention to provide a non-invasive retinal scanning system that detects blood loss by measuring the intensity of light reflected from selected points of the fundus region of the eye.

It is another object of the present invention to provide a non-invasive retinal scanning system wherein a plurality of readings are taken from a given patient over a given period of time thus allowing the patient in question to provide his or her own base line reference.

It is another object of the present invention to provide a non-invasive retinal scanning system that is sufficiently mobile to allow examination of multiple patients in separate rooms or facilities.

Other objects and advantages over the prior art will become apparent to those skilled in the art upon reading the detailed description together with the drawings as described as follows.

DISCLOSURE OF THE INVENTION

In accordance with the various features of this invention, a method and apparatus for monitoring blood loss via retinal venous oxygen saturation is provided which detect changes in the oxygen saturation of the retinal veins by non-invasive means when internal bleeding in a patient occurs. The apparatus, a non-invasive retinal scanning system, comprises a retinal scanner that illuminates a plurality of points on the fundus and detects reflectance and a signal processing means that uses reflectance spectrophotometry techniques to convert these reflected signals into resultant data points that can be stored or displayed. A decline in the value of these resultant data points indicates a drop in venous hemoglobin saturation that allows the user to determine the rate and estimate the volume of blood loss.

Applications for the present invention include monitoring trauma victims, postoperative patients for blood loss, and monitoring nontraumatic causes for internal bleeding, such as peptic ulcers. An additional feature of the present invention permits the user to monitor successful replacement of blood loss, for example, after transfusion.

Those skilled in the art will recognize that the appearance of the fundus varies between persons. Additionally, it will be understood that a certain degree of variation even exists between the eyes of a given subject. Thus, a major concept utilized in the present invention is that each patient serves as his own baseline saturation value. Clearly, the same eye should be used for all readings in order to maximize the accuracy of this technique.

BEST MODE FOR CARRYING OUT THE INVENTION

Figure 1:
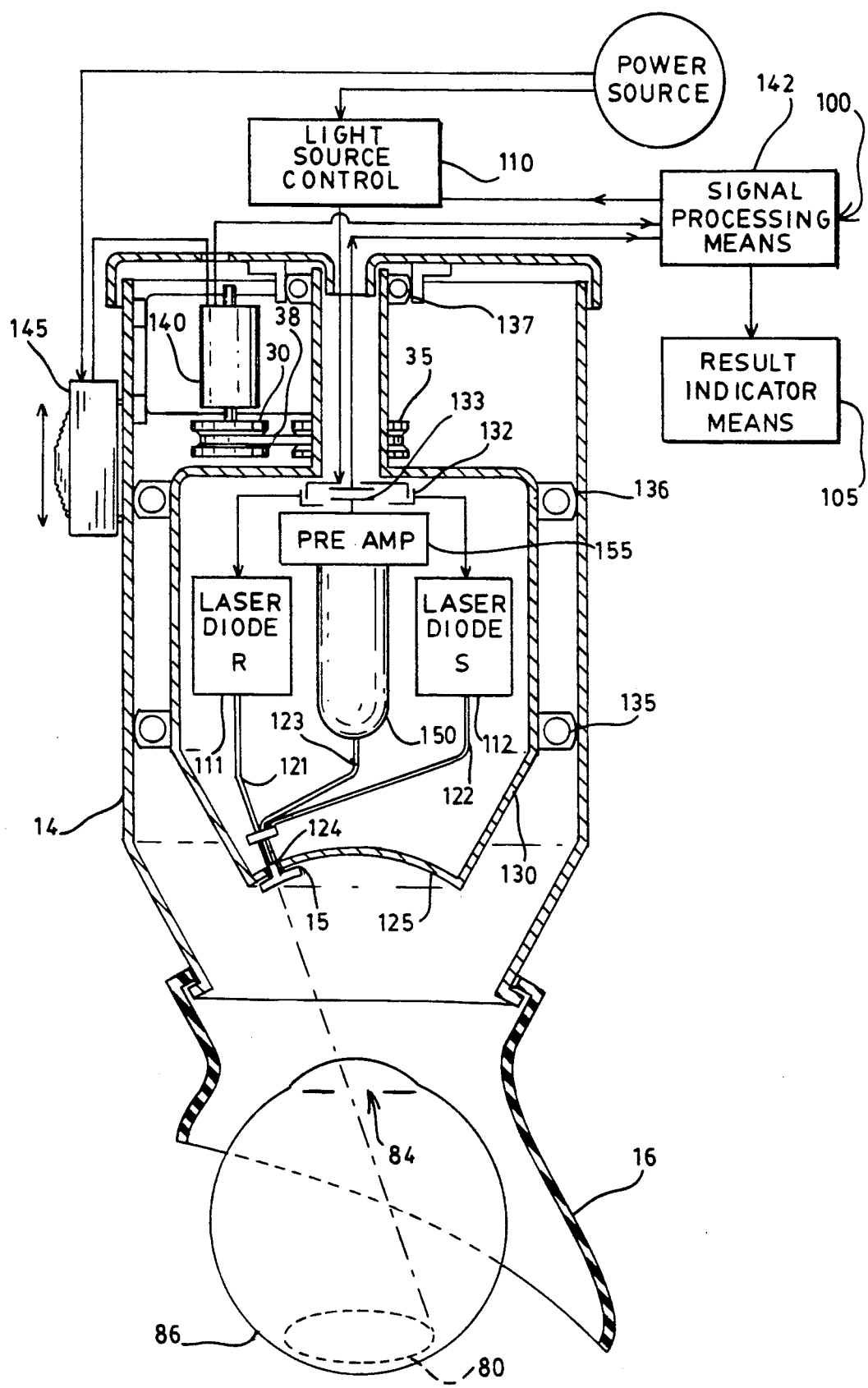
FIG. 1 is an illustration of a non-invasive retinal scanner for monitoring blood loss.
Figure 2:
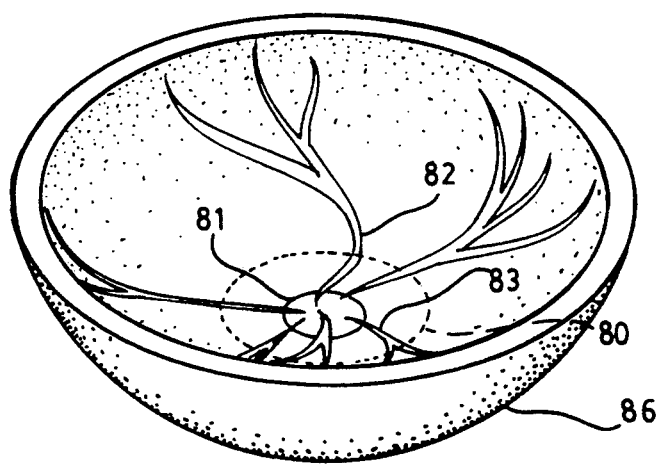
FIG. 2 represents the region of the fundus being scanned.

In this disclosure, the present invention employs a unique method of scanning the retinal surface for the venous oxygen saturation value. The posterior portion of the ocular fundus 86 in FIGS. 1 and 2 is illuminated. A retinal vein 82 and artery 83 emerge from the optic disc 81. Each dot in the ring of illumination 80 in the figure represents a point at which the retina is illuminated. The light source is oriented in such a fashion that an annulus of illumination is formed on the fundus, allowing venous blood to be scanned at one or more illumination points. Utilizing reflectance spectrophotometry, the intensity of illumination of the retinal veins is lower than that of the retinal arteries, and thus the values of interest are the low intensity ones after the thirty point annular scan is conducted. Areas of the dark, retinal pigment layer which are illuminated do not register in the scanning process.

Referring now to FIG. 1, an on-off switch 145 is triggered manually, which activates the motor 140. When speed detection means 142 detects that the motor has reached about one hundred and twenty (120) rpms, the light source control device 110, in a feedback fashion, activates the laser diodes 111 and 112, which emit a reference and sample wavelength, respectively. The reference wavelength is in the range of about 700 to about 710 nanometers, with the preferred wavelength being about 710 nanometers, whereas the sample wavelength is in the range of about 670 to about 680 nanometers, with the preferred wavelength being about 670 nanometers. In the preferred embodiment, the laser diodes pulsate alternately thirty times each in 0.5 second. Electrical wiring from the light source control is rotatably attached to the diodes by slip rings 132 permitting the wiring to rotate with the diodes from that junction. Emissions from the reference and sample laser diodes are then interfaced with optical fibers 121 and 122, respectively. These fibers 121 and 122 are oriented at an angle to the main axis of the internal housing 130. The detector fiber 123 is grouped with the other fibers in the same orientation. Those skilled in the art will recognize the necessity of preventing cross-talk between emission and detector fibers. In the preferred embodiment each fiber is painted black to prevent cross-talk between emission and detector fibers. The wall 125 of the internal housing, which in the illustrated preferred embodiment is concave, is opaque except for the small opening 124. This aperture is of a selected dimension such that light transmission at the fiberoptic terminus is permitted. In the illustrated preferred embodiment an optical glass cap 15 covers the glass fibers. The motor 140 is equipped with drive means to permit the internal housing 130, which contains the laser diodes, photodetector, and optical fibers, to rotate about an axis. In the preferred embodiment, selected pulleys 30 and 35 and a belt 38 are utilized to drive the internal housing at a preselected speed, in the preferred embodiment about one hundred and twenty (120) rpms. Those skilled in the art will recognize that a geared shaft drive mechanism would also serve to rotate the internal housing at a preselected speed about an axis. Bearings 135, 136 and 137 allow the internal housing 130 to rotate while the external housing 14 remains stationary.

An optic cup 16, made of opaque rubber in the preferred embodiment, rests on the periorbital rim of the subject. With the contralateral eyelid closed, the pupils dilate, allowing the fundus to be illuminated only by the light sources, 111 and 112. Their light paths pass through the pupil 84. As the light sources rotate, they form a ring of illumination 80 on the retinal vasculature. The reflected light at each point on the ring of illumination 80 of illumination for both the reference and sample wavelengths is received by the optical fiber 123 attached to the photodetector 150. Each signal of intensity is in turn amplified by the photodetector amplifier 155. Since the photodetector rotates, the output signal from the amplifier 155 must be carried by wiring with a slip ring junction 133.

Signal processing means 100 retrieve the reflected reference and reflected sample signals. The reflected signals are processed and the results displayed to the operator by display means 105. The display means may as preferred display a signal proportional to the oxygen saturation of venous hemoglobin or may display the rate of change of oxygen saturation of venous hemoglobin. If desired the results can also be saved by the signal analysis means. The reflected signals are split into two signals by signal division means 94 at both the sample and the reference wavelengths. A filter means 96 shown in FIG. 4 eliminates noise from the signal flow. Next, reflected signal amplification means 98 amplifies the difference between reflected sample and reflected reference signals. The result indicator means 105 indicates the result to the operator in the desired manner. As the low signals represent venous oxygen saturation, these are the values plotted on the display graph, FIG. 3. A decrease in the value of subsequent signals is indicative of a state of blood loss. The rate of change of oxygen saturation of venous hemoglobin is the function that alerts the operator of a state of blood loss in a patient and also indicates the quantity of blood loss. This signal analysis means is constructed of spectrophotometry components well known in the art.

In the typical example of a patient who has just sustained blunt trauma to the abdomen, and injury to the spleen is suspected clinically, the present invention enables the user to obtain a value of venous oxygen saturation at five to ten minute intervals. The minimum interval of time for monitoring a patient is one minute, because an intact cardio-respiratory system requires at least this long to re-oxygenate the entire blood pool. This value is then plotted on a graph, represented by FIG. 3. The Y-axis refers to the venous oxygen saturation, which corresponds to the fall in total blood volume. The X-axis plots these serial measurements over time.

Figure 3:
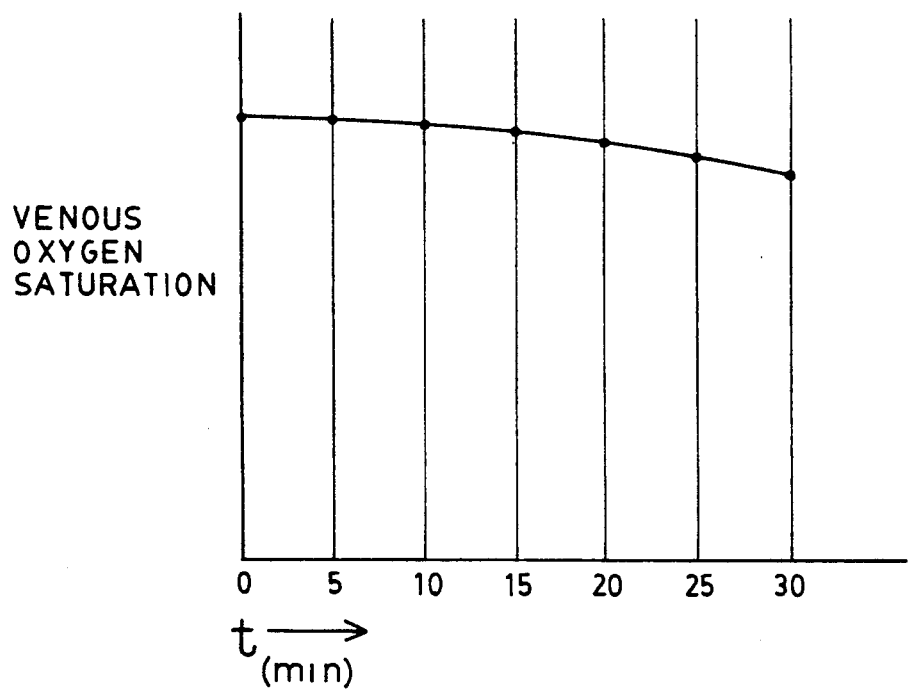
FIG. 3 is a graph of changes in venous oxygen saturation over time. This corresponds to losses in total blood volume.
Figure 4:
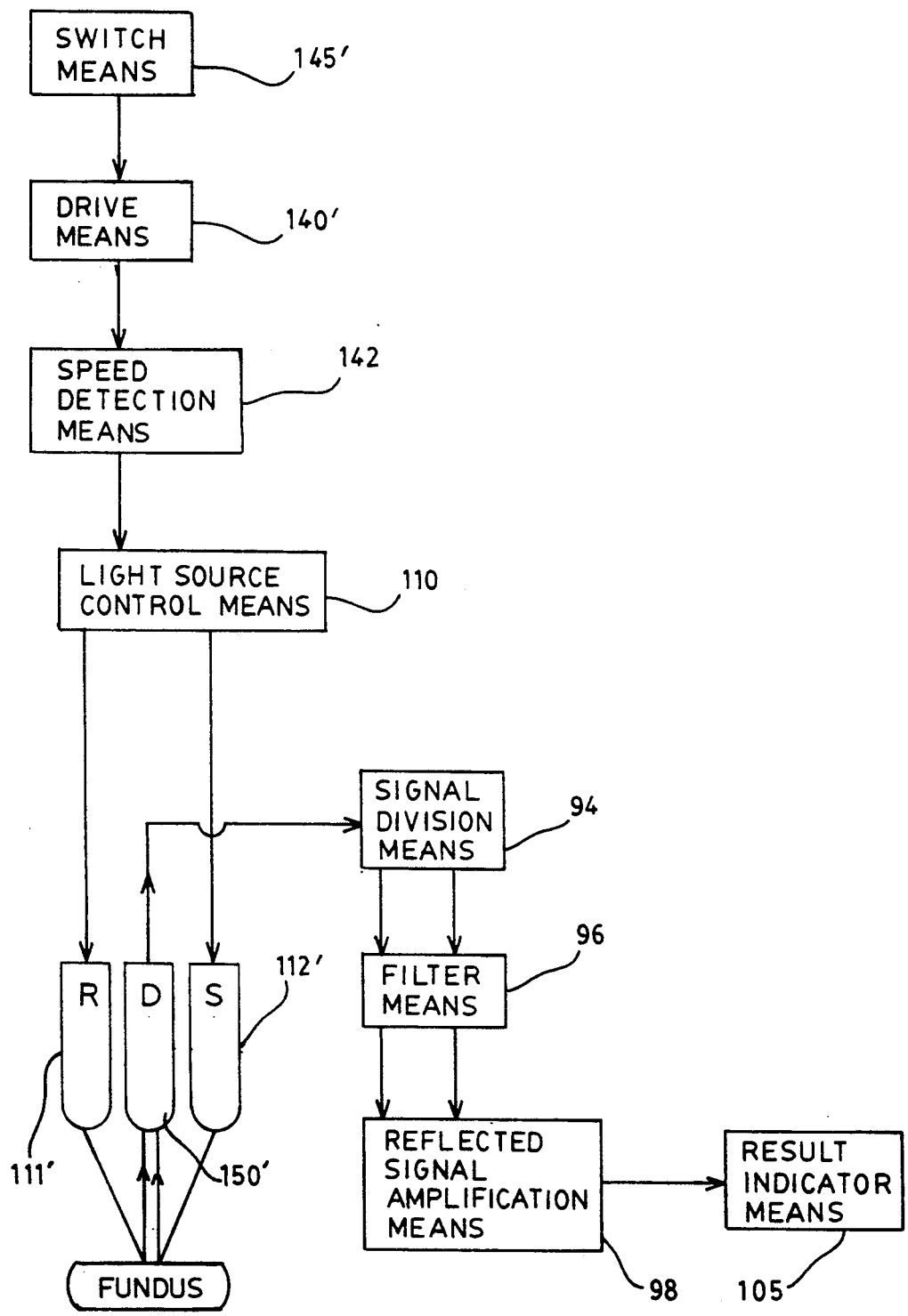
FIG. 4 is a block diagram of the apparatus of the present invention.

Certain patients will stabilize and have no further bleeding from their injured spleen. Other patients, however, will continue to bleed as depicted in FIG. 3. When the slope of the curve increases to a predetermined value, this alerts the surgeon that blood leaking from the splenic injury is advancing from a slow to a rapid rate. At that point, the patient is taken promptly to surgery to arrest the bleeding long before shock develops.

Monitoring every five to ten minutes enables the user to monitor alternately several patients with a single device, such as in the intensive care, recovery room setting, or emergency department setting. Patient identification means and data storage means allow the operator to monitor blood loss in a plurality of patients.

From the foregoing description, it will be recognized by those skilled in the art that a non-invasive retinal scanning system for monitoring blood loss offering advantages over the prior art has been provided. Specifically, the method and apparatus for monitoring blood loss via retinal venous oxygen saturation provides non-invasive means for measuring blood loss early by measuring the intensity of light reflected from selected points of the fundus region of the eye, such that a change in the oxyhemoglobin saturation of the vein can be detected when 1% or less of total blood volume has been lost, thus allowing detection of blood loss prior to the onset of shock. Further the present invention provides a non-invasive blood loss detection method wherein a plurality of readings are taken from a given patient over a given period of time thus allowing the patient in question to provide his or her own base line reference. The present invention is sufficiently mobile to allow examination of multiple patients in separate rooms or facilities.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, I claim:

1. A non-invasive retinal scanning system for detecting blood loss by measuring venous hemoglobin saturation by illuminating a portion of the fundus, said scanning system comprising:
   a retinal scanner for illuminating a plurality of points on said fundus, said retinal scanner having light generating means for generating a reference signal of a selected frequency and a sample signal of a selected frequency, light source control means for selectively alternating the activation of said reference signal and said sample signal, light detecting means for detecting said reference light signal and said sample light signal reflected by said fundus, an internal housing unit for containing said light generating and said light detecting means, drive means for rotating said internal housing about an axis at a selected speed and an external housing unit containing said internal housing unit and said drive means;
   signal processing means for processing said reflected reference and said reflected sample light signals whereby a signal proportional to the oxygen saturation of venous hemoglobin is produced;
   result indicator means for indicating to an operator the rate of change of oxygen saturation of venous hemoglobin; and
   speed detection means whereby said light source control means is activated in a feedback fashion when said drive means achieves a preselected speed.

2. The non-invasive retinal scanning system of claim 1 wherein aid retinal scanner further comprises a light shielding means in cooperation with said external housing for blocking out extraneous light and thereby dilating a patient's pupil to allow the fundus to be illuminated only by said reference and said sample signals.

3. The non-invasive retinal scanning system of claim 1 wherein said retinal scanning system is portable and said retinal scanner is handheld.

4. The non-invasive retinal scanning system of claim 1 wherein said retinal scanner further comprises a switch means for selectively activating said drive means.

5. A non-invasive retinal scanning system for detecting blood loss by measuring venous hemoglobin saturation by illuminating a portion of the fundus, said scanning system comprising:
   light generating means for generating a reference signal and a sample signal;
   light source control means for selectively alternating the activation of said reference signal and said sample signal;
   light detecting means for detecting said reference light signal and said sample light signal reflected by said fundus;
   an internal housing unit for containing said light generating and said light detecting means;
   drive means for rotating said internal housing about an axis at a selected speed;
   a switch means for selectively activating said drive means;
   a speed detection means whereby said light source control means is activated in a feedback fashion when said drive means achieves a preselected speed;
   an external housing unit containing said internal housing unit and said drive means;
   a light shielding means in cooperation with said external housing for blocking out extraneous light and thereby dilating a patient's pupil to allow the fundus to be illuminated only by said reference and said sample signals; and
   a signal processing means for splitting said reflected reference signal and said reflected sample signals, filtering out noise, and amplifying the difference between said reflected reference signal and said reflected sample signals whereby a signal proportional to the oxygen saturation of venous hemoglobin is produced; and
   result indicator means for indicating to an operator the rate of change of oxygen saturation of venous hemoglobin.

6. The non-invasive retinal scanning system of claim 5 wherein said signal processing means further comprises patient identification means and patient hemoglobin saturation value storage means whereby a plurality of patients may be simultaneously monitored.

* * * * *